United States Patent
Abel et al.

(10) Patent No.: US 11,710,543 B2
(45) Date of Patent: Jul. 25, 2023

(54) METHODS FOR PREDICTING AN ACTIVE SET OF COMPOUNDS HAVING ALTERNATIVE CORES, AND DRUG DISCOVERY METHODS INVOLVING THE SAME

(71) Applicant: Schrödinger, Inc., New York, NY (US)

(72) Inventors: Robert L. Abel, Brooklyn, NY (US); Lingle Wang, New York, NY (US); Sathesh Bhat, Jersey City, NJ (US); Sayan Mondal, New York, NY (US); Jeremy Robert Greenwood, Brooklyn, NY (US); Kyle Konze, New York, NY (US)

(73) Assignee: Schrödinger, Inc., New York, NY (US)

( * ) Notice: Subject to any disclaimer, the term of this patent is extended or adjusted under 35 U.S.C. 154(b) by 273 days.

(21) Appl. No.: 16/757,298

(22) PCT Filed: Oct. 18, 2018

(86) PCT No.: PCT/US2018/056486
§ 371 (c)(1),
(2) Date: Apr. 17, 2020

(87) PCT Pub. No.: WO2019/079580
PCT Pub. Date: Apr. 25, 2019

(65) Prior Publication Data
US 2021/0217500 A1      Jul. 15, 2021

Related U.S. Application Data

(60) Provisional application No. 62/574,346, filed on Oct. 19, 2017.

(51) Int. Cl.
G16C 20/50     (2019.01)
G16C 10/00     (2019.01)
(Continued)

(52) U.S. Cl.
CPC ............. *G16C 20/50* (2019.02); *G16C 10/00* (2019.02); *G16C 20/10* (2019.02); *G16C 20/70* (2019.02)

(58) Field of Classification Search
CPC ........ G16C 20/50; G16C 20/10; G16C 20/70; G16C 10/00; G16B 15/30
See application file for complete search history.

(56) References Cited

U.S. PATENT DOCUMENTS 6,900,228 B1 * 5/2005 Carroll ............... A61K 31/4468
514/329
2005/0164167 A1 * 7/2005 Buscher .................. C12Q 1/70
435/5
(Continued)

FOREIGN PATENT DOCUMENTS

EP      1452868           9/2004
EP      1452868 A2 * 9/2004 ............. G01N 33/68
(Continued)

OTHER PUBLICATIONS

Abel et al., "Advancing Drug Discovery through Enhanced Free Energy Calculation," Accounts of Chemical Research, Jul. 5, 2017, 50(7): 1625-1632.
(Continued)

*Primary Examiner* — Son T Le
*Assistant Examiner* — Lal C Mang
(74) *Attorney, Agent, or Firm* — Fish & Richardson P.C.

(57) ABSTRACT

A system, device, and method for predicting an active set of compounds that bind to a biomolecular target is disclosed. The system and device contain modules allowing for the prediction of an active set of compounds. A core identification module can identify the core of an initial lead compound. A core hopping module is used to identify potential lead compounds having different cores compared to the core of an initial lead compound. A scoring module (Continued)

can use computational techniques to calculate the relative binding free energy of each identified potential lead compound. An activity prediction module can use the relative binding free energy calculations to predict an active set of compounds that bind to the biomolecular target. Empirical analysis can be used to inform the accuracy and completeness of the predicted active set of compounds.

9 Claims, 9 Drawing Sheets

(51) Int. Cl.
*G16C 20/10* (2019.01)
*G16C 20/70* (2019.01)

(56) References Cited

U.S. PATENT DOCUMENTS

| | | | | |
|---|---|---|---|---|
| 2009/0287465 | A1* | 11/2009 | Shenkin | G06G 7/58 |
| | | | | 703/12 |
| 2010/0273664 | A1* | 10/2010 | Lange | C40B 30/02 |
| | | | | 506/8 |
| 2013/0226549 | A1* | 8/2013 | Tseng | G06F 19/12 |
| 2015/0178442 | A1* | 6/2015 | Abel | G06F 19/12 |
| 2018/0012129 | A1* | 1/2018 | Bhaduri | G06N 5/02 |

FOREIGN PATENT DOCUMENTS

| | | |
|---|---|---|
| JP | 2006-323833 | 11/2006 |
| JP | 2007-137887 | 6/2007 |
| JP | 2017-509039 | 3/2017 |
| JP | 2017-091180 | 5/2017 |
| WO | WO 200039751 | 7/2000 |
| WO | WO-2000039751 A * | 7/2000 ............... G06N 7/00 |

OTHER PUBLICATIONS

Bohm H-J et al., "Scaffold hopping," Drug Discovery Today: Technologies, Dec. 1, 2004, 1(3):217-224.
EP Extended European Search Report in Eurpoean Appln. No. 18868894.9, dated Nov. 30, 2020, 11 pages.
Hu et al., "Recent Advances in Scaffold Hopping : Mini perspective," Journal of Medicinal Chemistry, Dec. 21, 2016, 60(4):1238-1246.
Maass et al., "Recore: A Fast and Versa'ile Method for Scaffold Hopping Based on Small Molecule Crystal Structure Conformations," Journal of Chemical information and Modeling, Feb. 17, 2007, 47(2):390-399.
Sheng et al., "Fragment Informatics and Computational Fragment-Based Drug Design: An Overview and Update," Medicinal Research Reviews, May 19, 2012, 33(3):554-598.
Vainio et al., "Scaffold Hopping by Fragment Replacement," Journal of Chemical Information and Modeling, Jul. 2013, 53(7):1825-1835.
PCT International Search Report and Written Opinion in International Appln. No. PCT/US2018/56486, dated Dec. 12, 2008, 9 pages.
PCT Preliminary Report on Patentability in International Appln. No. PCT/US2018/056486, dated Apr. 30, 2020, 8 pages.
Wang et al., "Accurate Modeling of Scaffold Hopping Transformations in Drug Discovery," Journal of Chemical Theory and Computation, Nov. 23, 2016, 13(1):42-54.
Office Action in Japanese Appln. No. 2020-521863, dated Nov. 29, 2022, 15 pages (with English translation).

* cited by examiner

METHODS FOR PREDICTING AN ACTIVE SET OF COMPOUNDS HAVING ALTERNATIVE CORES, AND DRUG DISCOVERY METHODS INVOLVING THE SAME

TECHNICAL FIELD

This application relates generally to using a computer to assist in predicting an active set of compounds for binding to a target biomolecule by strategically modifying an initial lead compound known to bind to the target biomolecule, and relates more specifically to predicting the active set of compounds by computationally and empirically changing the core region of the initial lead compound known to bind to the target biomolecule.

BACKGROUND

Biomolecules often serve particular functions and the ability to modulate the functionality of a biomolecule can be useful for treating diseases and for engineering industrial biomolecular applications. The functionality of a biomolecule is sometimes modulated by whether and how one or more ligands are bound to the biomolecule. For example, biomolecules often have regions (e.g., an "active site") where one or more ligands can bind to the biomolecule and thereby modulate the functionality of the biomolecule. Therefore, scientists and engineers are interested in identifying potential lead compounds that can act as ligands and modulate the functionality of biomolecules. Frequently, scientists and engineers are aware of an initial lead compound that binds to a biomolecular target, but are hoping to find other compounds with similar or higher binding affinity (e.g., a compound that binds more tightly than the initial lead compound). One way to identify potential lead compounds with higher binding affinity than an initial lead compound is to identify compounds that are similar to the initial lead compound by varying the chemistry in particular regions of the initial lead compound. Variations in the initial lead compound may lead to stronger binding affinity by strengthening an existing contact with the biomolecular target (such as a salt bridge or a hydrophobic interaction) or even by creating a new contact with the biomolecular target. Both empirical (i.e., experimental "wet lab" methods) and computational techniques can be used for identifying potential lead compounds that are similar to the initial lead compound. Likewise, both empirical and computational techniques can be used to calculate the binding affinities of potential lead compounds that are similar to the initial lead compound.

SUMMARY

One aspect features a method of identifying a plurality of potential lead compounds. The method includes analyzing an initial lead compound known to bind to a biomolecular target. The analysis involves partitioning the initial lead compound, using a computer system, into atoms defining a lead compound core and atoms defining a lead compound non-core. A plurality of alternative cores is identified, using a computer system, to replace the lead compound core in the initial lead compound, thereby generating a plurality of potential lead compounds each having a respective one of the plurality of alternative cores. The difference in binding free energy between the initial lead compound and each potential lead compound (the relative binding free energy) is calculated using a computer system. The method also includes predicting whether each potential lead compound will bind to the biomolecular target and identifying a predicted active set of potential lead compounds based on the prediction, using a computer system.

Another aspect features a non-transitory computer readable storage medium that includes a computer readable program that when executed on a computer causes the computer to predict whether potential lead compounds will bind to a biomolecular target. Making the prediction as to whether potential lead compounds will bind to a biomolecular target involves performing various steps, including analyzing an initial lead compound known to bind to a biomolecular target (using a core identification module stored in memory and coupled to at least one processor). The analyzing of the initial lead compound includes partitioning the initial lead compound into atoms defining a lead compound core and atoms defining a lead compound non-core. As another step, a plurality of alternative cores is identified to replace the lead compound core (using a core hopping module stored in memory and coupled to at least one processor), thereby generating a plurality potential lead compounds each having a respective one of the plurality of alternative cores. As another step, a difference in binding free energy between the initial lead compound and each potential lead compound is calculated using a scoring module stored in memory and coupled to at least one processor. As another step, a prediction is made as to whether each potential lead compound will bind to the biomolecular target; the prediction is made using an activity prediction module stored in memory and coupled to at least one processor.

Another aspect features a computer system that has at least one processor, a core identification module, a core hopping module, a scoring module, and an activity prediction module. The core identification module is stored in memory and coupled to at least one processor, and is programmed to receive information identifying an initial lead compound known to bind to a biomolecular target, and to analyze the initial lead compound. The analysis includes portioning the initial lead compound into atoms defining a lead compound core and atoms defining a lead compound non-core. The core hopping module is stored in memory and coupled to at least one processor, and is programmed to identify a plurality of alternative cores to replace the initial lead compound core, thereby generating a plurality of potential lead compounds each having a respective one of the plurality of alternative cores. The scoring module is stored in memory and coupled to at least one processor, and is programmed to calculate a difference in binding free energy between the initial lead compound and each potential lead compound. The activity prediction module is stored in memory and coupled to at least one processor, and is programmed to provide a prediction of whether a potential lead compound will bind to the biomolecular target.

In some implementations, a synthesized set of at least some of the potential lead compounds of the predicted active set is obtained (i.e., a first set of synthesized potential lead compounds) and an activity is empirically determined for each of the first set of synthesized potential lead compounds. In some implementations, the empirically determined activity of each of the first set of synthesized potential lead compounds is compared to a threshold activity level.

Similarly, in some implementations, a synthesized set of at least some of the potential lead compounds predicted to not bind with the biomolecular target is obtained (i.e., a second synthesized set of potential leady compounds) and an activity is empirically determined for each of the second set of synthesized potential lead compounds. In some implementations, the empirically determined activity of each of the second set of synthesized potential lead compounds is compared to a pre-determined activity level.

In some implementations, the initial lead compound is partitioned using a retrosynthetic analysis of the initial lead compound.

In some implementations, the plurality of alternative cores are chosen from a database of synthetically feasible cores.

In some implementations, the generation of at least one potential lead compound includes creating an additional covalent bond or annihilating an existing covalent bond, or both creating an additional first covalent bond and annihilating an existing second covalent bond different from the first covalent bond.

The difference in binding free energy can be calculated using a free energy perturbation technique. The free energy perturbation technique can use a soft bond potential to calculate a bonded stretch interaction energy of existing covalent bonds for annihilation and additional covalent bonds for creation.

DETAILED DESCRIPTION

Figure 1:
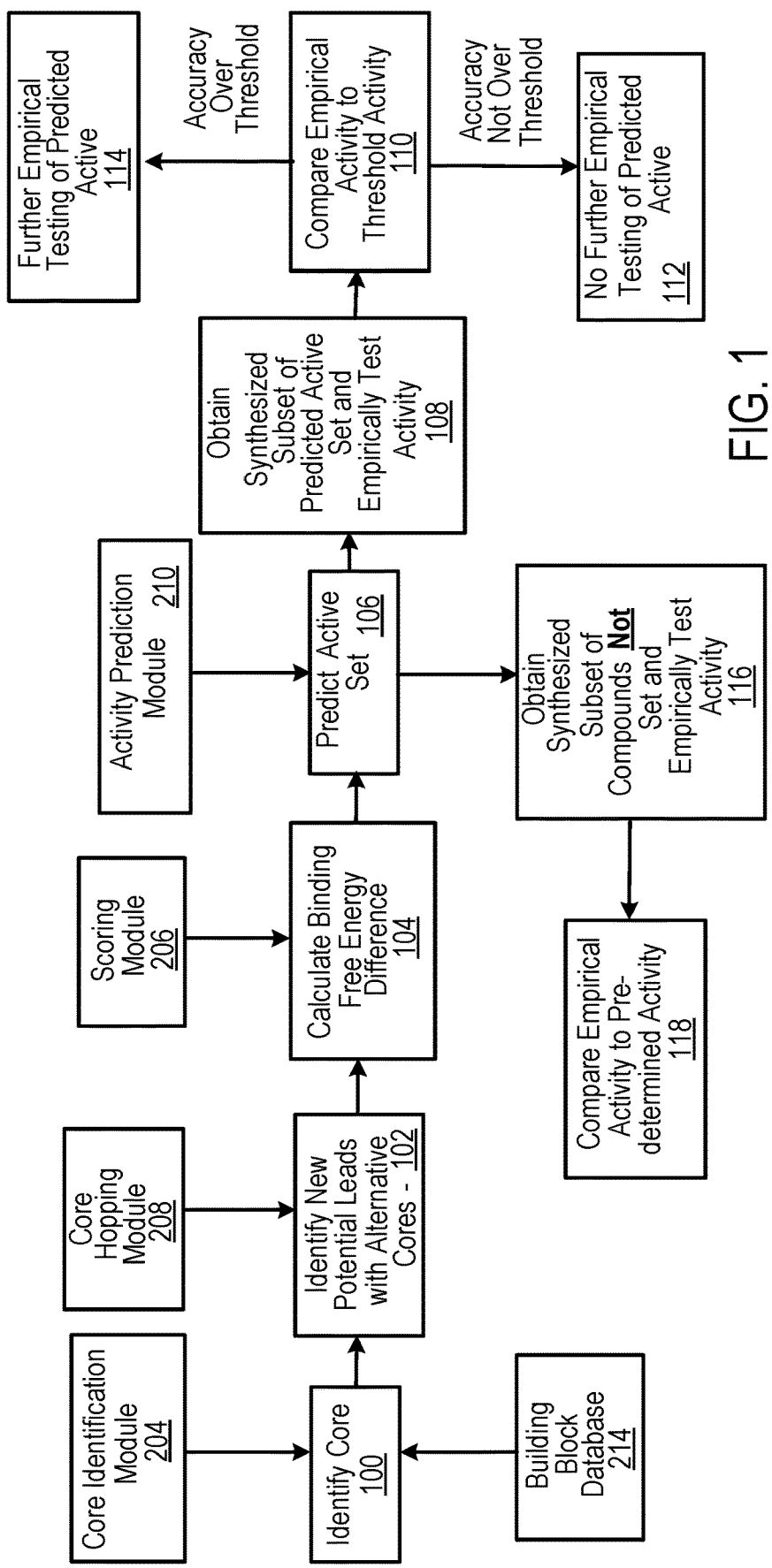
FIG. 1 is a block/flow diagram showing a method of identifying an active set of potential lead compounds.

Given an initial lead compound, it is often useful to identify similar compounds to the initial lead compound (i.e., a set of potential lead compounds) because certain variations of the initial lead compound may lead to a potential lead compound that (i) has higher binding affinity than the initial lead compound itself, (ii) is more commercially viable, (iii) is metabolized in a safer way than the initial lead compound itself, (iv) is not covered by the same intellectual property rights as the initial lead compound, etc. One technique for identifying potential lead compounds is core hopping, which involves partitioning an initial lead compound into a core region and one or more non-core regions (where the non-core regions contain peripheral chemical motifs/moieties called R-groups), and then substituting the core region with a different core, thereby creating an altered version of the lead compound.

Computers can help reduce the cost and time involved in enumerating potential lead compounds. Computational approaches to enumerating potential lead compounds typically focus on the non-core region of a molecule—they focus on exploring the effects of changing one or more peripheral R-groups in an initial lead compound. However, since the peripheral R-groups frequently interact with the biomolecular target, it can be beneficial to at least initially preserve those peripheral R-groups and instead focus on the effects of changing the core of the lead compound (a process called "core hopping"). Additionally, it may be useful to change the core region of an initial lead molecule if the core region of the initial lead compound is toxic when metabolized. Unfortunately, changing the core of an initial lead compound often involves forming and/or annihilating multiple covalent bonds, which can make it difficult to accurately calculate the binding free energy difference between an initial lead compound and a potential lead compound. The prediction system and methods disclosed herein focus on identifying potential lead compounds using core hopping, including core hopping that involves forming and/or annihilating multiple covalent bonds.

The prediction system and methods disclosed herein also focus on calculating the binding free energy difference between an initial lead compound and potential lead compounds, where the potential lead compounds are enumerated using core hopping. The binding affinity may be determined empirically (i.e., experimentally in a "wet lab"), computationally on a computer, or both. Testing the binding affinity of a compound empirically is costly, as it involves synthesizing the compound and performing time-consuming binding assays. Computers can help reduce the cost and time involved in determining binding affinity. There are many ways to predict the binding affinity of a particular compound computationally, e.g., calculating the free energy of binding, which can be used to predict whether binding is likely to occur at any given temperature. The relative difference in binding free energies between an initial lead compound and a potential lead compound can also be calculated using computational techniques.

Among other advantages, the techniques and tools disclosed here describe how computational methods, sometimes combined with chemical synthesis and empirical testing in the wet lab, can use core hopping and free energy calculations to accurately predict an active set of potential lead compounds with high binding affinities to a biomolecular target. The ability to predict a complete set of active potential lead compounds based on the disclosed techniques and tools is an unexpected result; the accuracy and usefulness of conventional computational predictions related to drug design and biomolecular binding events may be questionable.

Figure 4A:
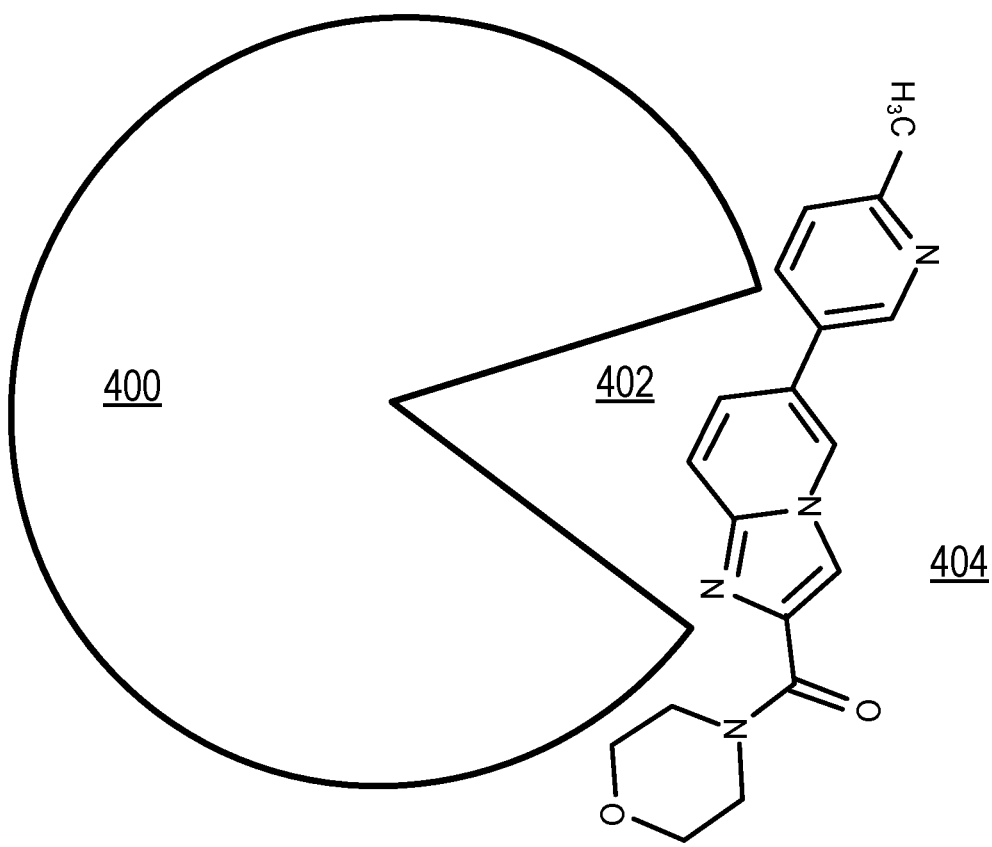
FIG. 4A is a cartoon of a biomolecular target binding with an initial lead compound.
Figure 4B:
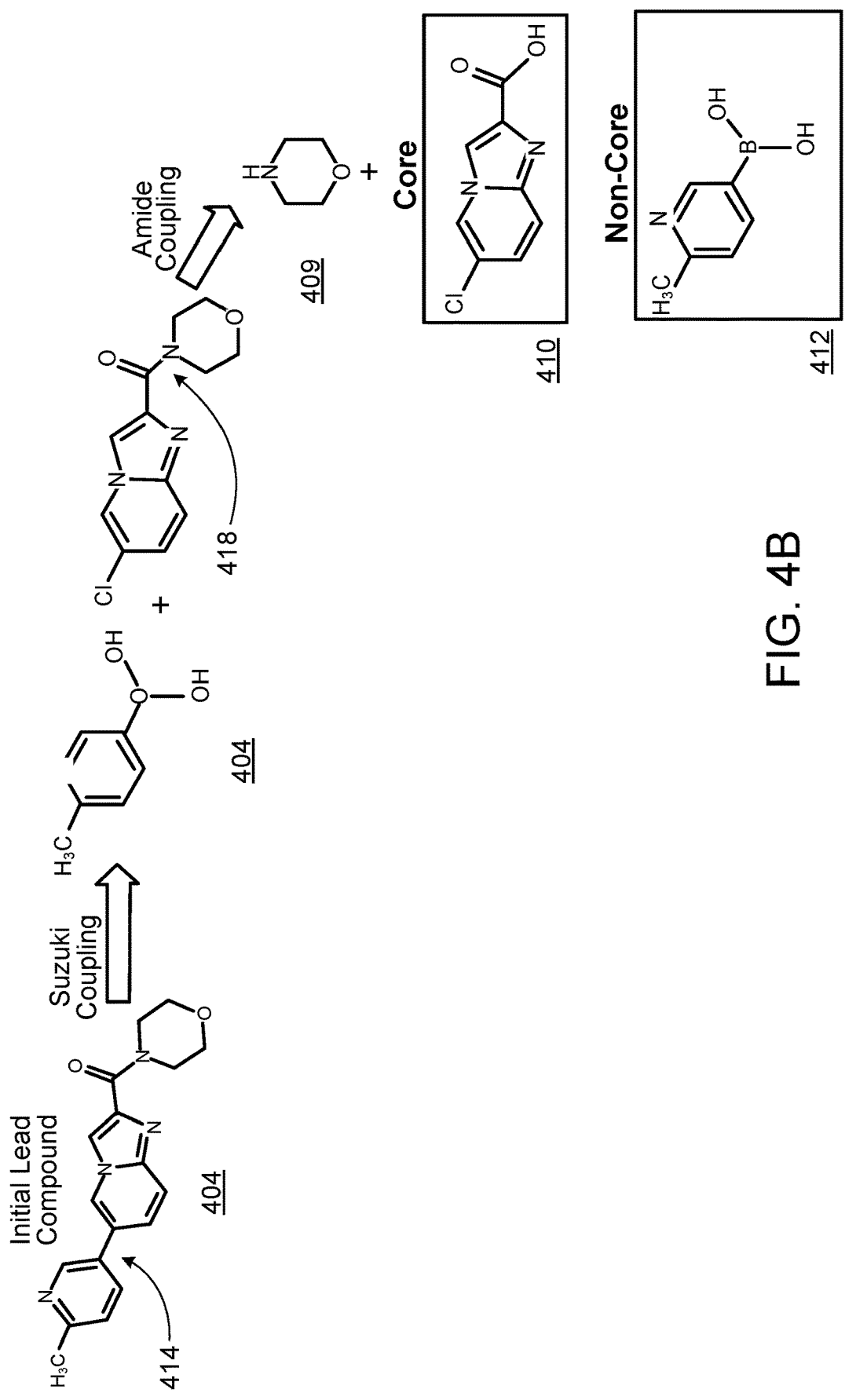
FIG. 4B is a flow diagram showing one example of a method for identifying a core of an initial lead compound.

FIG. 1 shows a block/flow diagram illustratively depicting a method for identifying a plurality of potential lead compounds, where blocks 100 to 118 (outlined in bold) represent steps of the method. Referring to FIG. 1 and FIGS. 4A-B, the first step 100 of the method involves identifying a core 410 in an initial lead compound 404 using core identification module 204. The initial lead compound 404 is a compound that is either known to or suspected to bind to an active site 402 of a biomolecular target 400. The step 100 of identifying a core 410 can be performed using a variety of methods, such as retrosynthetic analysis, machine learning (e.g., by using a training set of known compounds and their identified cores), etc. Alternatively, the step 100 of identifying the core 410 can be accomplished by receiving information about a pre-identified core 410. The atoms in the initial lead compound 404 that do not form part of the core 410 are part of the non-core 412, and in this way the initial lead compound 404 is partitioned into atoms defining a lead compound core 410 and atoms defining a lead compound non-core 412.

One advantage of using retrosynthetic analysis to identify a core 410 is that retrosynthetic analysis allows one to partition a molecule into fragments that are amenable to chemical reactions. FIG. 4B is an example of how retrosynthetic analysis can identify a core 410 in a synthetically-aware fashion. A database 300 of known reactions (FIG. 3) can be used to identify fragments that may be removed from the initial lead compound 404 by computationally cleaving bonds in a synthetically-aware fashion. In the example in FIG. 4B, the initial lead compound 404 is first electronically cut at covalent bond 414 because this allows the initial lead compound 404 to be divided into two functionalized fragments (a boronic acid fragment 406 and a halide fragment 408) that can serve as reactants in a Suzuki Coupling reaction yielding lead compound 404 as a reaction product. Next, the covalent bond 418 of the halide fragment 408 is computationally cleaved because this allows the halide fragment 408 to be divided into two fragments (morpholine fragment 409 and core fragment 410) that can serve as reactants in an amide coupling reaction yielding the halide fragment 408 as a reaction product. When the core identification module 204 can no longer find any bonds that may be computationally cleaved in a synthetically aware manner (i.e., no more reactions in the database 300 of known reactions are applicable), the core identification module 204 ends the retrosynthetic analysis process and identifies the most internal fragment as the core (i.e., the fragment connected to the highest number of other fragments).

Alternatively, the core 410 can be identified by comparing the initial lead compound 404 to a set of cores known to exist in other compounds, e.g., the compounds in building block database 214 can be a set of known cores. If any of the known cores in building block database 214 are identified in the initial lead compound 404, then that identified region of the initial lead compound 404 can serve as the core 410. There may be one or more cores 410 identified, in which case the process described in FIG. 1 can be performed on each and every identified core 410, and could even be performed on both cores simultaneously. With the core 410 identified, retrosynthetic analysis can be used as previously described to partition the initial lead compound 404 into non-core fragments 412 in a synthetically-aware manner.

Many other methods can be used to partition the initial lead compound 404 into a core 410 and non-core fragments 412. For example, the building block database 214 may include not only a set of known cores 410, but may also include a set of R-groups known to exist in successful drug candidates. In that situation, the initial lead compound 404 can be searched for the known R-groups in database 214 and the parts of the initial lead compound 404 containing known R-groups can be labeled as the non-core 412, while the remainder of the initial lead compound 404 can be labeled as the core 410. If this method is used, then retrosynthetic analysis would not be used, although reaction database 300 could be used to winnow down the R-groups identified in the initial lead compound 404 into only synthetically feasible R-groups.

Figure 5:
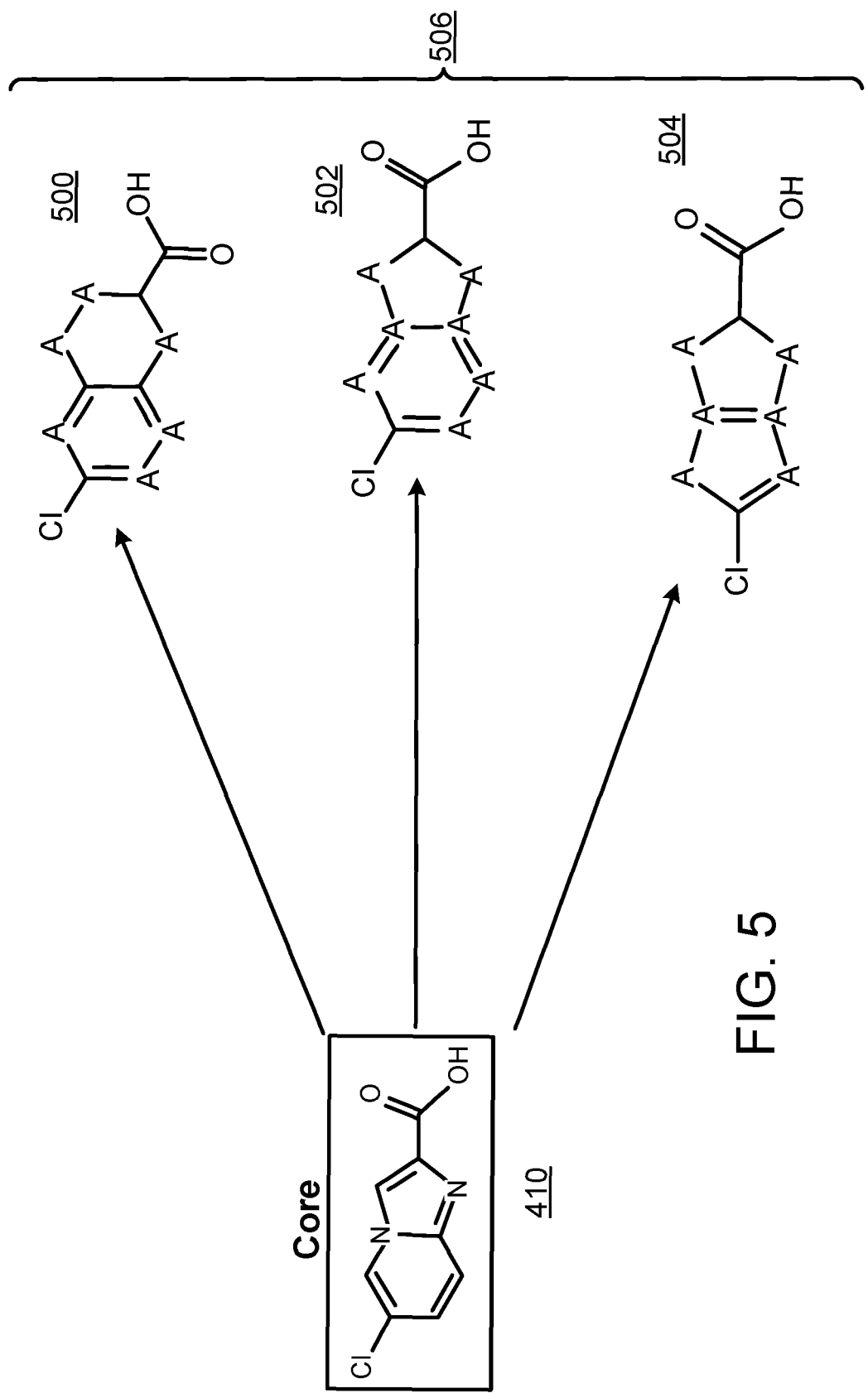
FIG. 5 is a diagram showing the core identified in the initial lead compound in FIG. 4 and examples of alternative cores.

The next step of the process shown in FIG. 1 is step 102, identifying new potential lead compounds with alternative cores, which first involves identifying a plurality of alternative cores 506 (see FIG. 5). Step 102 can be accomplished using a core hopping module 208. The plurality of alternative cores 506 can be chosen from a building block database 214, where the building block database 214 includes commercially available compounds that may serve as alternative cores. A plurality of alternative cores 506 can be chosen from the compounds in the building block database 214 based on whether a compound is amenable to the same or similar chemistry as in core 410, e.g., whether a compound has similar functional groups, size and topology to the lead compound core 410. For example, compounds can be deemed to have similar chemistry as core 410 if they possess reaction sites that can re-form the broken chemical bonds (e.g., bonds 414 and 418) that link the core 410 to the non-core fragments 412, through the same or similar chemical reactions used in the retrosynthetic analysis (e.g., Suzuki Coupling and amide coupling reactions in FIG. 4B) during step 100. Furthermore, compounds can be deemed to have a similar chemistry as core 410 if they possess the capacity to host the non-core fragments 412 while keeping the non-core fragments 412's relative positions approximately equivalent to their relative positions in the initial lead compound 404. Various algorithms exist to make these kinds of comparisons. For example, QSAR (Quantitative Structure Activity Relationship) methodologies can be used to convert a molecular structure into a vector of features that can be compared with another molecule's vector of features.

A plurality of potential lead compounds 600 with alternative cores can then be generated by electronically replacing the core 410 with one of the alternative cores 506 (e.g., for core 410, the core hopping module 208 can identify alternative cores 500, 502, 504, etc.) having similar chemistry as the core 410. As such, the non-core of the initial lead compound 404 can remain the same, while the core 410 of the initial lead compound 404 can be changed (e.g., by replacing it with an alternative core, such as alternative core 502). If retrosynthetic analysis was used to partition the initial lead compound into a core 410 and non-core 412, then the replacement of core 410 of the initial lead compound 404 with alternative cores 506 can be done using the retrosynthetic analysis reactions that were originally used by the core identification module 204 when identifying the core in step 102. Ultimately, the set of potential lead compounds 600 can be equal in number to the number of previously-identified alternative cores 506, although the set of potential lead compounds 600 may be winnowed down based on a user-provided metric (e.g., molecular weight, drug-likeness, predicted or known toxicity, predicted or known ADME properties, etc.). While FIG. 6 only shows eight potential lead compounds 600, it will be understood that there could be dozens, hundreds, or more than a thousand potential lead compounds 600.

The next step shown in FIG. 1 is step 104, which involves calculating the binding free energy difference between the initial lead compound 404 and each of the potential lead compounds 600. In order to predict the binding free energy difference between the initial lead compound 404 and each potential lead compound 600, a scoring module 206 can be used. The difference in binding free energy can be calculated using a variety of techniques, e.g., free energy perturbation (FEP), thermodynamic integration, and umbrella sampling.

As described herein, FEP can be used to calculate transformation free energy differences $\Delta F_{a \to b}$ attributable to alchemical changes associated with bond-breaking and bond formation. Such alchemical changes are relevant to many core-hopping modifications that involve changing the bond topologies of the core 410 of the initial lead compound 404.

Such modifications include, for example, transforming a linear molecule into a ring structure (ring opening/closing), changing the size of a ring structure (ring size change), extending a single ring into a fused ring or a bridged ring (ring extension), etc.

In general, the transformation free energy difference $\Delta F_{a \to b}$ between two states a and b can be expressed by:

$$\Delta F_{a \to b} = -\frac{1}{2} \ln \langle \exp\{-\beta[\mathcal{H}_b(x, p_x) - \mathcal{H}_a(x, p_x)]\} \rangle_a \quad (1)$$

where $\beta^{-1} = k_B T$, $k_B$ is the Boltzmann constant and T is the temperature. $\mathcal{H}_a(x, p_x)$ and $\mathcal{H}_b(x, p_x)$ are the Hamiltonians characteristic of states a and b, respectively. Here, state a can be the initial lead compound 404 and state b can be one of the potential lead compounds 600. Calculating accurate free energy differences can include introducing a coupling parameter lambda, $\lambda$, that varies from 0 (state a) to 1 (state b). The free energy difference between state a and state b (with Hamiltonians $\mathcal{H}(\lambda=0)=\mathcal{H}_0$ and $\mathcal{H}(\lambda=1)=\mathcal{H}_1$, respectively) is calculated by smoothly changing the Hamiltonian from $\mathcal{H}_0$ to $\mathcal{H}_1$. The relationship between the Hamiltonians of the two states is as follows:

$$\mathcal{H}(1-\lambda) = (1-\lambda)\mathcal{H}_a + \lambda \mathcal{H}_b \quad (2)$$

The introduction of the coupling parameter $\lambda$ allows the transition from state a to state b to be broken up into individual windows representing various states along the transition pathway from a to b. A "window" usually consists of a molecular dynamics simulation performed with the coupling parameter, $\lambda$, at a specific fixed value. In this way, FEP "perturbs" the system from state a to state b. For example, transforming the initial lead compound 404 into one of the potential lead compounds 600 may include creating and/or annihilating bonds, and the creation and annihilation of bonds can be performed in increments of small "perturbations" over each $\lambda$ window. For example, changing core 410 into core 500 involves the addition of a chemical bond in order to transform the 5-membered ring into a 6-membered ring, and also involves the annihilation of certain double-bounds in the 5-membered ring of core 410. This bond creation and bond annihilation and be accomplished by slowly changing the coupling parameter $\lambda$ over many individual simulations.

The free energy differences between neighboring $\lambda$ windows can be summed in order to arrive at the relative free energy difference between state a (the initial lead compound) and state b (a potential lead compound). Consequently, the transformation free energy difference $\Delta F_{a \to b}$ between state a and state b can be calculated by:

$$\Delta F_{a \to b} = -\frac{1}{\beta} \ln \langle \exp\{-\beta[\mathcal{H}(\lambda=1) - \mathcal{H}(\lambda=0)]\} \rangle_{\lambda=0} = \quad (3)$$
$$-\frac{1}{\beta} \sum_{i=0}^{N-1} \ln \langle \exp\{-\beta[\mathcal{H}(x, p_x; \lambda_{i+1}) - \mathcal{H}(x, p_x; \lambda_i)]\} \rangle_i$$

where N is the number of windows between the initial state ($\lambda=0$) and the final state ($\lambda=1$), and $\lambda_i$ represents the values of the coupling parameter in the initial, intermediate and final states. The relative free energy difference between neighboring $\lambda$ windows can be calculated using a variety of methods, e.g., the Bennett Acceptance Ratio method.

Classical mechanics forcefields (e.g., CHARMM, OPLS, GROMOS and AMBER) typically use a harmonic potential to model the bond stretch interactions between two atoms:

$$U_{bs}(r) = \frac{1}{2} k(r - r_0)^2 \quad (4)$$

where k is the force constant and $r_0$ is the equilibrium distance. When calculating alchemical free energy differences in FEP, the harmonic potential is typically scaled linearly via the coupling parameter $\lambda$:

$$U_{bs}(\lambda, r) = \frac{1}{2} \lambda k(r - r_0)^2 \quad (5)$$

When the distance between the two atoms is very large, the harmonic potential asymptotically approaches infinity (i.e., a singularity exists on the potential energy surface), resulting in potential numerical instability when performing alchemical FEP simulations. A soft bond potential can be used to resolve the numerical instability when creating or annihilating bonds:

$$U_{bs}(\lambda, r) = \frac{1}{2} kf(\lambda)(r - r_0)^2 \frac{1}{\left(1 + g(\lambda)\alpha(k, \lambda)(r - r_0)^2\right)} \quad (6)$$

where the functions $f(\lambda)$, $g(\lambda)$, and $\alpha(k, \lambda)$ are each continuous functions and simultaneously satisfy the following conditions: $f(\lambda=0)=0$; $f(\lambda=1)=1$; $g(\lambda=0)=1$; $\alpha(k, \lambda<1)>0$. When $f(\lambda)=\lambda$, $g(\lambda)=1-\lambda$, and $\alpha(k, \lambda)=\alpha=$const (a constant number), the soft bond potential is:

$$U_{bs}(\lambda, r) = \frac{1}{2} \lambda k(r - r_0)^2 \frac{1}{\left(1 + a(1 - \lambda)(r - r_0)^2\right)} \quad (7)$$

The soft bond potential removes the numerical instability problems associated with the singularity on the potential energy surface that exists in the typical harmonic potential. Therefore, the soft bond potential can be used to smoothly turn on and off the bond stretch interactions that are introduced or annihilated when transforming the initial lead compound 404 into one of the potential lead compounds 600 during an FEP simulation.

Figure 7:
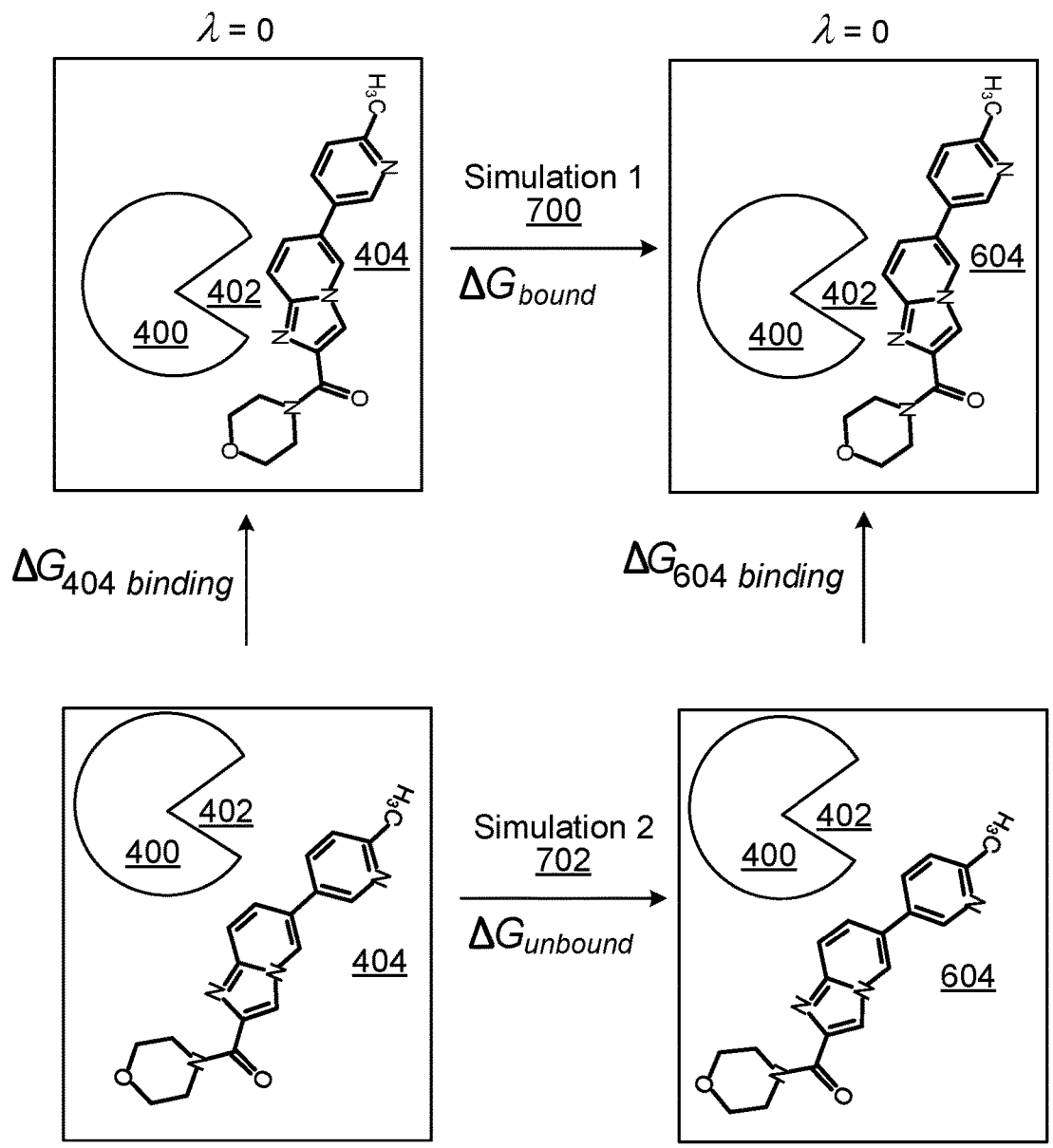
FIG. 7 is example of how free energy perturbation and molecular dynamics simulations can be used to calculate the difference in binding free energies between two different compounds.

Referring to FIG. 7, to calculate the relative binding free energy $\Delta\Delta G$ between the initial lead compound 404 and a potential lead compound (e.g., compound 604), two FEP molecular dynamics simulations (using classical/Newtonian mechanics) can be performed, each yielding a transformation free energy difference $\Delta G$ (or $\Delta F$ if an NVT ensemble is used)—the first simulation 700 can transform the initial lead compound 404 into potential lead compound 604 while the initial lead compound 404 is in the binding site 402; the second simulation 702 can transform the initial lead compound 404 into the potential lead compound 604 while the initial lead compound 404 and the unbound biomolecule are in bulk solvent. As indicated in FIG. 7, when $\lambda=0$ the initial lead compound 404 is being simulated, when $\lambda=1$ the potential lead compound 604 is being simulated, and when $0>\lambda>1$, intermediate states are simulated. In practice, the unbound biomolecular target need not be simulated in simulation 702, since it exists in the same unbound form regardless of the value of $\lambda$.

Both simulations 700 and 702 can use the soft bond potential (Eq. 6) to model the bond stretch interactions between two atoms. The transformation free energy change ΔG associated with each simulation can then be calculated according to Eq. 3. The difference between the two free energy changes calculated from simulations 700 and 702 ($\Delta G_{bound}$ and $\Delta G_{unbound}$, respectively) provides the relative binding free energy ΔΔG of the initial lead compound 404 compared to the potential lead compound 604, as shown in the equation in box 704. Once the relative binding free energy ΔΔG is determined for each of the potential lead compounds 600, the scoring module 206 can be used to rank each of the potential lead compounds 600 based on their calculated relative binding free energy ΔΔG.

The molecular dynamics simulations used in step 104 can be performed using a variety of different forcefields (such as the default forcefields used in the CHARMM, OPLS, GROMACS, and AMBER software packages). The statistical ensemble for the simulations can be any appropriate ensemble, e.g., NPT (constant temperature and pressure) or NVT (constant temperature and volume). Before performing the simulations, the user can provide the system 200 with physical parameters, e.g., pH, temperature, and salt concentration. The starting structure 226 for the first simulation 700 can be provided from the results of an empirical technique, e.g., x-ray crystallography or NMR. The simulations may involve restraints (e.g., harmonic restraints) in order to ensure that the initial lead compound 404 maintains its approximate position in the active site 402 as it alchemically transitions into each potential lead compound 600.

Figure 6:
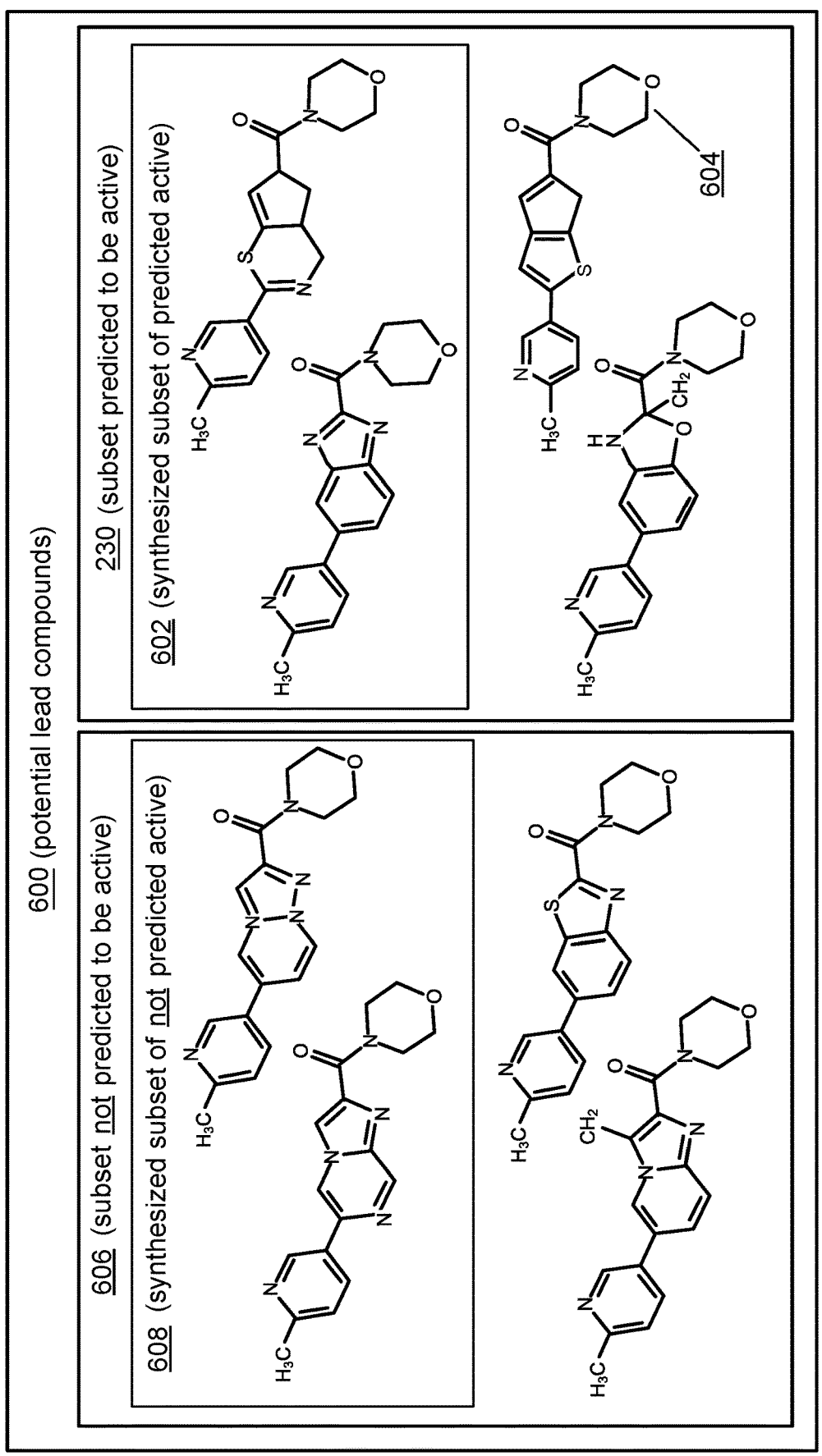
FIG. 6 shows examples of potential lead compounds derived from the alternative cores of the initial lead compound shown in FIG. 5.

Referring to FIGS. 1 and 6, the next step shown in FIG. 1 is step 106, which involves predicting an active set 230 of the potential lead compounds 600 using the previously calculating relative binding free energy ΔΔG from step 104. For example, the activity prediction module 210 can determine that the top ranking potential lead compounds 600 from the scoring module 206 are predicted to be active, e.g., the top 25% based on the calculated ΔΔG values. Alternatively, a pre-determined ΔΔG cut-off can be used, such as any value lower than zero (a ΔΔG value lower than zero indicates that the potential lead compound 600 is a better binder that the initial lead compound 404).

While FIG. 6 only shows four potential lead compounds in the predicted active set 230, it will be understood that there could be dozens, hundreds, or more than a thousand compounds in the predicted active set 230. The activity prediction module 210 may predict activity based on only the calculated relative binding free energy ΔΔG from the scoring module 206, or the activity prediction module 210 could take into account other factors beyond just the calculated relative binding free energy ΔΔG, e.g., predicted/known ADME properties and toxicity. Ultimately, the output of the activity prediction module 210 is the predicted active set 230 (which may include 1D, 2D, or 3D chemical structures, chemical names, and other information for each compound in the predicted active set 230).

In some embodiments, the method can also comprise obtaining a synthesized set of at least some of the potential lead compounds of the predicted active set 230 (i.e., a first set 602 of synthesized potential lead compounds 600), as symbolized in step 108 of FIG. 1. While FIG. 6 only shows two potential lead compounds 602 chosen for synthesis and empirical testing, it will be understood that there could be dozens, hundreds, or more than a thousand compounds chosen for synthesis. Once the first synthesized set 602 is obtained, the activity of each of the potential lead compounds in the first synthesized set 602 can be empirically determined, as symbolized in step 108. Any number of empirical techniques in the wet lab can be used to empirically determine the activity of each of the potential lead compounds in the first synthesized set 602, e.g., calorimetry, electrophoresis, ELISA, fluorescence changes, etc.

Once the empirically determined activity of potential lead compounds in the first synthesized set 602 is obtained, the empirically determined activity can be compared with a threshold activity, as shown in step 110 of FIG. 1. The comparison can be used to determine whether the predicted active set 230 is accurate. Comparing the empirically determined activity can involve comparing the difference in the empirically determined activity for a potential lead compound 600 and the initial lead compound 404, since such a comparison is more easily related to the previously calculated relative binding free energy ΔΔG. As such, the activity threshold is actually a threshold for the difference between the activity of a potential lead compound 600 and the initial lead compound 404.

The threshold activity can be any pre-determined activity value (e.g., a value representing a difference in activity of the initial lead compound 404 compared to the potential lead compound 600). The comparison of the empirically determined activity with a threshold activity can be used to determine which compounds should be in the predicted active set 230 based on the empirically determined activity, which can then be used to calculate the accuracy of the predicted active set 230. For example, if 1 out of 100 potential lead compounds in the first synthesized set 602 are not deemed active from empirical analysis (e.g., as determined by whether the compounds meet the pre-determined activity cutoff) then the predicted active set 230 would be calculated to be approximately 99% accurate. Another method to test the accuracy of the predicted active set 230 is by calculating the correlation coefficient ($r^2$) of the predicted activity versus empirical activity of the first synthesized set 602. As shown in step 114 of FIG. 1, if the accuracy of the first synthesized set 602 is over a pre-determined threshold, then some or all of the compounds in the predicted active set 230 can be empirically tested for clinical efficacy (e.g., efficacy in a mouse model). However, if the accuracy of the predicted active subset 602 is under the pre-determined threshold, then the compounds in the predicted active set 230 may ultimately not be empirically tested for clinical efficacy (see step 112 of FIG. 1).

In some embodiments, the method can also comprise determining the completeness of the predicted active set 230, where a predicted active set 230 is deemed incomplete if there are compounds not predicted to be active (compounds in subset 606) that are in fact empirically determined to be active (see step 116 of FIG. 1). The completeness of the predicted active set 230 can be determined by first obtaining a synthesized set of at least some of the potential lead compounds 606 not predicted to be active (i.e., a second set 608 of synthesized potential lead compounds), as shown in step 116 of FIG. 1. Once the second synthesized set 608 is obtained, the activity of each of the compounds in the second synthesized set 608 (step 116 of FIG. 1) can be empirically determined. Any number of empirical techniques in the wet lab can be used to empirically determine the activity of each of the potential lead compounds in the second synthesized set 608, e.g., calorimetry, electrophoresis, ELISA, fluorescence changes, etc.

As shown in step 118, once the empirically determined activity of the compounds in the second synthesized set 608 is obtained, the empirically determined activity can be compared with the same pre-determined cutoff used in step 106. Comparing the empirically determined activity can involve comparing the difference in the empirically determined activity for a potential lead compound 600 and the initial lead compound 404, since such a comparison is more easily related to the previously calculated relative binding free energy difference ΔΔG. As such, the pre-determined cutoff is actually a cutoff for the difference between the activity of a potential lead compound 600 and the initial lead compound 404. If any of the compounds in the second synthesized set 608 are empirically found to be active when compared to the pre-determined cutoff, then the predicted active set 230 can be labeled as incomplete and the extent of incompleteness can be calculated. For example, if 1 out of 100 compounds in the second synthesized set 608 are active (e.g., as determined by whether the compounds are equal to or greater than the pre-determined activity cutoff) then the predicted active set 230 would be considered to be approximately 99% complete.

A number of embodiments of the claimed methods have been described. Nevertheless, it will be understood that various modifications can be made without departing from the spirit and scope of the claims. For example, FIG. 1 shows that all of the potential lead compounds 600 are identified (step 102) before any of the relative binding free energy differences are calculated (step 104); however, the potential lead compounds 600 may be identified serially and the relative binding free energy difference between a given identified compound and the initial lead compound 404 may be calculated before moving on to identifying the next potential lead compounds 600. As another example, FIG. 6 shows one conformation for each of the potential lead compounds 600, but each potential lead compound 600 may have multiple and distinct three-dimensional conformations, each of which could be analyzed using the steps disclosed in FIG. 1. As yet another example, FEP calculations described herein utilize classical molecular dynamics simulations, but could also be done using Monte Carlo simulations or QM/MM (quantum mechanics/molecular mechanics) simulations. Moreover, FEP calculations are not the only way to rank potential lead compounds based on their relative binding affinity; for example, scoring functions may also be used. Accordingly, other embodiments are within the scope of the claims.

Figure 2:
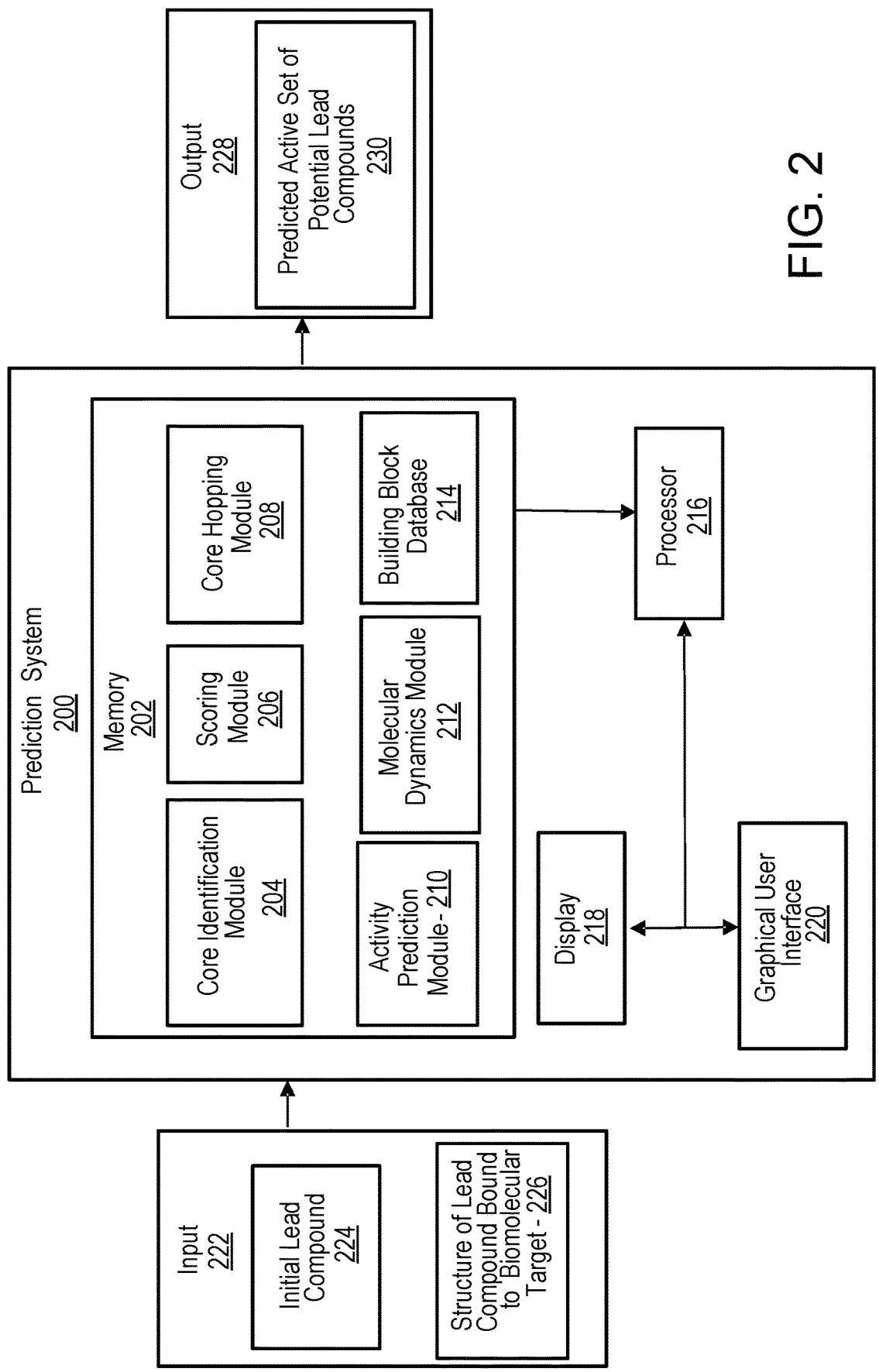
FIG. 2 is a block diagram showing a prediction system for identifying potential lead compounds.

Referring to FIG. 2, a computer prediction system 200 can be used for predicting a set of potential lead compounds 600 after receiving as input an initial lead compound 224 and the structure of the initial lead compound 224 bound to a biomolecular target 400 in the active site 402. The prediction system 200 can include one or more or processors 216 that are able to receive computer program instructions from a general purpose computer, special purpose computer, or any other programmable data processing apparatus. The one or more processors 216 are responsible for executing the received computer program instructions, e.g., instructions provided by modules stored in memory 202. The output 228 may be visualized on one or more displays 218 that are coupled to one or more graphical user interfaces 220. For example, the chemical structures of compounds in the predicted active set 230 can be shown on display 218 and the chemical structures can be manipulated and modified by a user via graphical user interface 220.

Figure 3:
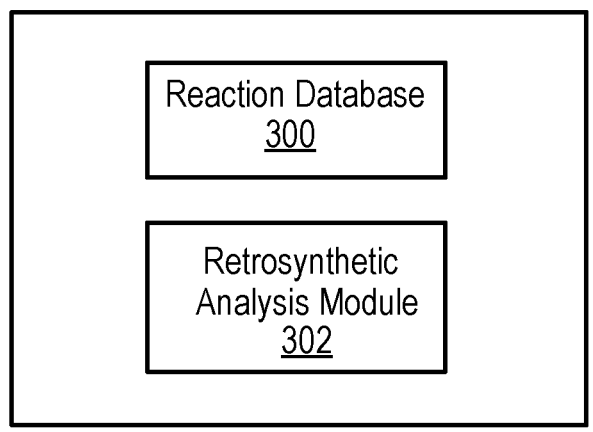
FIG. 3 is a block diagram showing one component of the prediction system shown in FIG. 2.

The prediction system 200 can have a memory 202 that stores information and/or instructions. The memory 202 can store a core identification module 204 that is coupled to at least one processor 216. The core identification module 204 can be programmed to receive information identifying an initial lead compound 404 that is known to bind to a biomolecular target 400 at the active site 402. Referring to FIGS. 2-4, the core identification module 204 can identify a core 410 within the initial lead compound 404, thereby partitioning the initial lead compound 404 into atoms defining a lead compound core 410 and atoms defining a lead compound non-core 412. The core identification module 204 can use various techniques to partition the initial lead compound 404, e.g., retrosynthetic analysis (FIG. 4B), machine learning, etc. If retrosynthetic analysis is used, then the core identification module 204 can have a retrosynthetic analysis module 302 and can have or be coupled to a reaction database 300 (see FIG. 3).

The memory 202 can also store a core hopping module 208 that is coupled to at least one processor 216. The core hopping module 208 can be programmed to identify a plurality of alternative cores 506 to replace the initial lead compound core 410. The core hopping module can receive the initial lead compound core 410 from the output of the core identification module 204. The alternative cores 506 can be identified by choosing them from one or more building block databases 214 containing information on various compounds that may serve as building blocks. The building block database 214 can be stored in memory (FIG. 2) and can also be accessed via the internet. The core hopping module 208 may identify any number of alternative cores 506, e.g., tens, hundreds, or more than a thousand alternative cores 506. In some implementations, the core hopping module 208 can choose only synthetically feasible alternative cores (i.e., cores that are amenable to chemical reactions with the non-core 412).

The core hopping module 208 can electronically replace the initial lead compound core 410 with alternative cores 506, thereby yielding a set of potential lead compounds 600 with alternative cores (FIG. 6). The replacement of the initial lead compound's core 410 with alternative cores 506 can be done using the retrosynthetic analysis reactions that were originally used by the core identification module 204 when identifying the core. The set of potential lead compounds 600 can be equal in number to the number of previously-identified alternative cores 506, although the set of potential lead compounds 600 may be winnowed down based on a user-provided metric (e.g., molecular weight, predicted or known toxicity, predicted or known ADME, etc.). Additionally, each potential lead compound 600 may have more than one three-dimensional conformation, each of which can be treated as a distinct potential lead compound.

The memory 202 can also store a scoring module 206 that is coupled to at least one processor 216. The scoring module 206 can receive information identifying the set of potential lead compounds 600, either from the core hopping module 208, as user input, or from another module besides the core hopping module 208. The scoring module 206 can then calculate the relative binding free energy ΔΔG between the initial lead compound 404 and each potential lead compound in the set of potential lead compounds 600. For example, the scoring module 206 can contain, be part of, or be coupled to a molecular dynamics module 212. The molecular dynamics module 212 can be used to conduct a simulation 700 of the transformation of the initial lead compound 404 into each potential lead compound 600 while the initial lead compound 404 is in the binding site 402, and can also be used to conduct a simulation 702 of the transformation of the initial lead compound 404 into each potential lead compound 600 while the initial lead compound 404 and the protein are in bulk solvent (see FIG. 7). Before performing the simulations, the user can provide the system 200 with physical parameters, e.g., pH, temperature, and salt concentration. The physical parameters can be provided by a user as input 222 for the prediction system 200. Once the molecular dynamics simulations 700 and 702 are performed, the relative binding free energy ΔΔG can then be calculated according to equation in box 704. The scoring module 206 can then rank each of the potential lead compounds 600 based on the calculated relative binding free energy ΔΔG.

The memory 202 can also store an activity prediction module 210 that is coupled to at least one processor. The activity prediction module 210 can receive information from the scoring module 206 related to the relative binding free energy ΔΔG of the initial lead compound 410 compared to each of the potential lead compounds 600 (e.g., snapshots from the trajectories in simulations 700 and 702, and the ranking of the potential lead compounds 600 based on their calculated relative binding free energy ΔΔG). The activity prediction module 210 can determine that the top ranking potential lead compounds 600 from the scoring module 206 are predicted active (e.g., using a pre-determined cutoff, such as a particular ΔΔG value, e.g., the ΔΔG value demarking the top 25%). The pre-determined cutoff can be provided by a user as input 222 for the prediction system 200. The pre-determined cutoff can be provided by a user as input 222 for the prediction system 200.

The prediction system 200 represents only one embodiment of a computer prediction system within the scope of this disclosure; other embodiments may include more or less input 222, more or less output 228, and more or less modules and components within the software and hardware of the prediction system. In addition, it will be understood that while FIG. 2 shows individual separate modules, any of the shown modules could in fact be a sub-module of any of the other shown modules. For example, as previously described, the molecular dynamics module 212 could be part of the scoring module 206. As another example, the activity prediction module 210 could be a sub-module of scoring module 206 and vice-versa.

Figure 9:
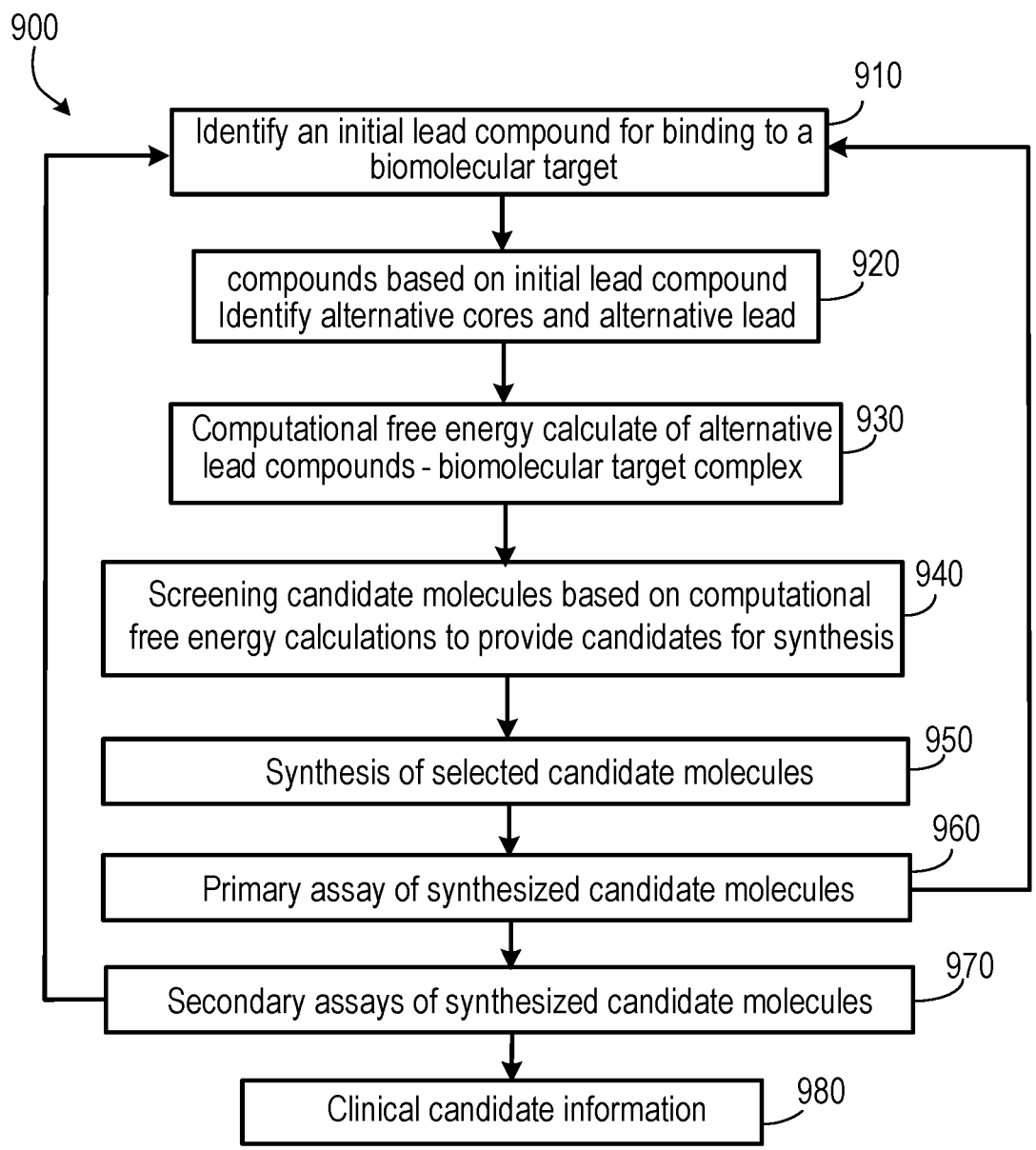
FIG. 9 is a flow chart illustrating steps in an exemplary drug design method that includes predicting active compounds having alternative cores.

In some embodiments, the methods of identifying lead compounds can be used to evaluate compounds in drug discovery. For example, the computational approaches described above can be used as a virtual filter for screening compounds for their suitability as a candidate for new pharmaceutical applications. Referring to FIG. 9, an exemplary drug design protocol 900 that incorporates these computational approaches is illustrated as a flow chart. Here, the process begins by identifying an initial lead compounds for binding to a biomolecular target (step 910). Typically, the biomolecular target is a protein, nucleic acid, or some other biological macromolecule involved in a particular metabolic or signaling pathway associated with a specific disease condition or pathology or to the infectivity or survival of a microbial pathogen. In some cases, the initial lead compounds are selected small molecules that are complementary to a binding site of the target. Examples of lead compounds can be molecules that are expected to serve as: receptor agonists, antagonists, inverse agonists, or modulators; enzyme activators or inhibitors; or ion channel openers or blockers. Initial lead compounds can be identified based on prior studies.

Based on the initial lead compound, a number of alternative cores to replace the lead compound core are identified using the techniques described above (step 920). Using the alternative cores, a number of candidate compounds are identified, each having one of the alternative cores. In some studies, a large number of candidate compounds (e.g., hundreds or thousands) are identified.

Once candidates are identified, computational free energy calculations are performed (step 930) to provide a measure of how strongly the candidate molecules will bind with the target. Generally, the computations are performed using a variety of techniques may be performed across a computer network. For example, the calculations may be performed using one or more servers that a researcher accesses via a network, such as the internet. The binding free energy difference between the initial lead compound and each potential lead compound is compared.

The results of the free energy calculations are used to screen the candidate molecules (step 940) in order to identify candidates for chemical analysis, which involves first synthesizing the candidate molecule (step 950) and then assaying the synthesized candidate molecules. Screening molecules can be performed by comparing the calculated free energy to a threshold value and/or by selecting those candidates that demonstrate the highest binding affinity to the biomolecular target compared to the initial lead compound and/or to other candidate molecules in the study.

Synthesis typically includes several steps including choosing a reaction pathway to make the compound, carrying out the reaction or reactions using suitable apparatus, separating the reaction product from the reaction mixture, and purifying the reaction product. Chemical composition and purity can be checked to ensure the correct compounds are assayed.

Generally, multiple different assays can be performed on each candidate molecule. For example, in step 960, primary assays can be performed from on all synthesized candidate molecules. The primary assays can be high throughput assays that provide a further screen for the candidate molecules rather that performing every necessary assay on every candidate compound selected from the computational screening step. Secondary assays (step 970) are performed on those molecules that demonstrate favorable results from the primary assays. Secondary assays can include both in vitro or in vivo assays to assess, e.g., selectivity and/or liability. Both the primary and secondary assays can provide information useful for identifying additional candidate molecules for further computational screening.

Candidate molecules with favorable results from the secondary assays can be identified as suitable candidates for further preclinical evaluation (step 980).

Similar applications in materials science are also feasible where the disclosed techniques may be used to compute the relative solvation free energies of different molecules for different solvent environments, there by optimizing the physical-chemical properties of the matter to be more suitable for the intended applications, for example.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, a data processing apparatus. Alternatively, or in addition, the program instructions can be encoded on an artificially-generated propagated signal, e.g., a machine-generated electrical, optical, or electromagnetic signal, that is generated to encode information for transmission to a suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) or LED (light emitting diode) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

Figure 8:
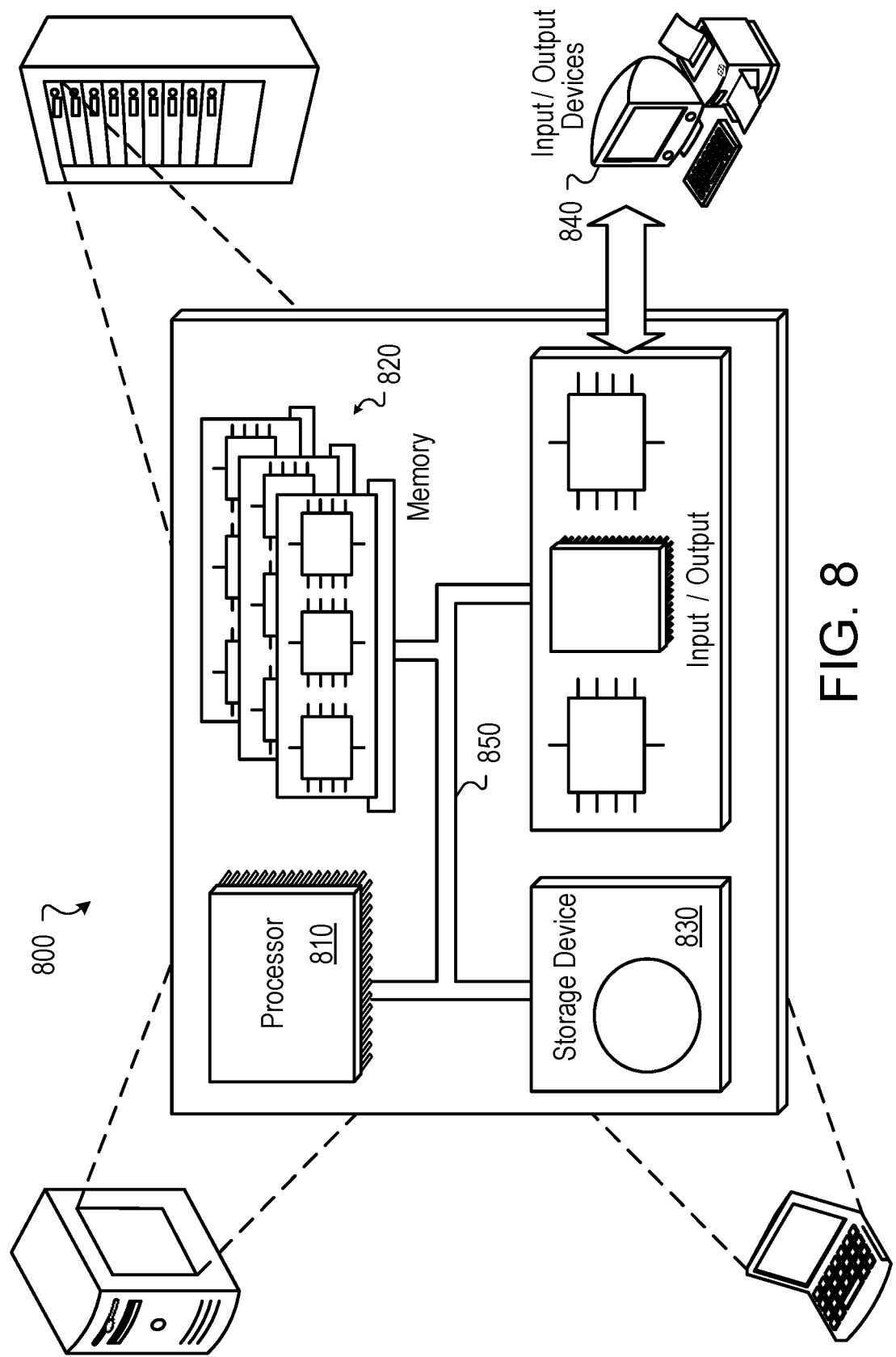
FIG. 8 is a diagram of a computer system.

An example of one such type of computer is shown in FIG. 8, which shows a schematic diagram of a generic computer system 800. The system 800 can be used for the operations described in association with any of the computer-implemented methods described previously, according to one implementation. The system 800 includes a processor 810, a memory 820, a storage device 830, and an input/output device 840. Each of the components 810, 820, 830, and 840 are interconnected using a system bus 850. The processor 810 is capable of processing instructions for execution within the system 800. In one implementation, the processor 810 is a single-threaded processor. In another implementation, the processor 810 is a multi-threaded processor. The processor 810 is capable of processing instructions stored in the memory 820 or on the storage device 830 to display graphical information for a user interface on the input/output device 840.

The memory 820 stores information within the system 800. In one implementation, the memory 820 is a computer-readable medium. In one implementation, the memory 820 is a volatile memory unit. In another implementation, the memory 820 is a non-volatile memory unit.

The storage device 830 is capable of providing mass storage for the system 800. In one implementation, the storage device 830 is a computer-readable medium. In various different implementations, the storage device 830 may be a floppy disk device, a hard disk device, an optical disk device, or a tape device.

The input/output device 840 provides input/output operations for the system 800. In one implementation, the input/output device 840 includes a keyboard and/or pointing device. In another implementation, the input/output device 840 includes a display unit for displaying graphical user interfaces.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

What is claimed is:

1. A method of screening potential lead compounds for suitability as a candidate for a pharmaceutical application, the method comprising the steps of:

analyzing, using a computer system, an initial lead compound known to bind to a biomolecular target involved in a metabolic or signaling pathway associated with a disease condition or pathology or to the infectivity or survival of a microbial pathogen, the analyzing comprising partitioning, by providing a database of known reactions, the initial lead compound into atoms defining a partitioned lead compound comprising a lead compound core and atoms defining a lead compound non-core, wherein the initial lead compound is partitioned using a computational retrosynthetic analysis of the initial lead compound;

identifying, using the computer system, a plurality of alternative cores to replace the lead compound core in the initial lead compound, thereby generating a plurality of potential lead compounds each having a respective one of the plurality of alternative cores;

calculating, using the computer system, a difference in binding free energy between the partitioned lead compound and each potential lead compound;

predicting, using the computer system, whether each potential lead compound will bind to the biomolecular target and identifying a predicted active set of potential lead compounds based on the prediction;

obtaining a synthesized set of at least some of the potential leads of the predicted active set to establish a first of potential lead compounds;

determining, empirically, an activity of each of the first set of synthesized potential lead compounds; and screening, based on the empirically determined activity, which of the synthesized potential lead compounds are suitable candidates for the pharmaceutical application.

2. The method of claim 1, further comprising obtaining a synthesized set of at least some of the potential lead compounds predicted to not bind with the biomolecular target to establish a second set of potential lead compounds and empirically determining an activity of each of the second set of synthesized potential lead compounds.

3. The method of claim 1, further comprising comparing the empirically determined activity of each of the first set of synthesized potential lead compounds with a threshold activity level.

4. The method of claim 2, further comprising comparing the empirically determined activity of each of the second set of synthesized potential lead compounds with a pre-determined activity level.

5. The method of claim 1, wherein the plurality of alternative cores are chosen from a database of synthetically feasible cores.

6. The method of claim 1, wherein the difference in binding free energy is calculated using a free energy calculation technique.

7. The method of claim 6, wherein the generation of at least one potential lead compound comprises creating an additional covalent bond or annihilating an existing covalent bond, or both creating an additional first covalent bond and annihilating an existing second covalent bond different from the first covalent bond.

8. The method of claim 7, wherein the free energy perturbation technique uses using a soft bond potential to calculate a bonded stretch interaction energy of existing covalent bonds for annihilation and additional covalent bonds for creation.

9. A method for pharmaceutical drug discovery, comprising:

identifying an initial lead compound for binding to a biomolecular target;

screening, with the method of claim 1, a predicted active set of potential lead compounds for binding to the biomolecular target based on the initial lead compound;

selecting one or more of the predicted active set of potential lead compounds for synthesis; and assaying the one or more synthesized selected compounds to assess each synthesized selected compounds suitability for in vivo use as a pharmaceutical compound.

* * * * *

UNITED STATES PATENT AND TRADEMARK OFFICE
CERTIFICATE OF CORRECTION

PATENT NO. : 11,710,543 B2
APPLICATION NO. : 16/757298
DATED : July 25, 2023
INVENTOR(S) : Robert L. Abel et al.

It is certified that error appears in the above-identified patent and that said Letters Patent is hereby corrected as shown below:

On the Title Page

In the references

In "OTHER PUBLICATIONS" on page 2, Column 2, Line 9, delete "Eurpoean" and insert -- European --.

In "OTHER PUBLICATIONS" on page 2, Column 2, Line 14, delete "Versa'ile" and insert -- Versatile --.

In the Specification

In Column 7, Line 13, delete "$k_B$ T," and insert -- $k_BT$, --.

In Column 7, Line 27, delete "$\lambda_b$" and insert -- $\lambda \mathcal{H}_b$ --.

In the Claims

Claim 6: In Column 18, Lines 39-40, delete "calculation" and insert -- perturbation --.

Signed and Sealed this
Twelfth Day of September, 2023

Katherine Kelly Vidal
*Director of the United States Patent and Trademark Office*